(12) United States Patent
Park et al.

(10) Patent No.: US 11,648,316 B2
(45) Date of Patent: May 16, 2023

(54) ORAL PHARMACEUTICAL COMPOSITION CONTAINING PEMETREXED AND PRODUCTION METHOD THEREOF

(71) Applicant: ICURE BNP CO., LTD., Geumwang-eup (KR)

(72) Inventors: Jin Woo Park, Seoul (KR); Young Ro Byun, Seoul (KR); Young Kweon Choi, Seoul (KR); Kwan Young Chang, Seoul (KR); Jae Bum Lee, Seoul (KR)

(73) Assignee: ICURE BNP CO., LTD., Geumwang-Eup (KR)

( * ) Notice: Subject to any disclaimer, the term of this patent is extended or adjusted under 35 U.S.C. 154(b) by 0 days.

(21) Appl. No.: 16/763,844

(22) PCT Filed: Oct. 10, 2018

(86) PCT No.: PCT/KR2018/011885
§ 371 (c)(1),
(2) Date: May 13, 2020

(87) PCT Pub. No.: WO2019/117441
PCT Pub. Date: Jun. 20, 2019

(65) Prior Publication Data
US 2021/0170036 A1   Jun. 10, 2021

(30) Foreign Application Priority Data

Dec. 13, 2017 (KR) .................. 10-2017-0171384

(51) Int. Cl.
*A61K 47/54* (2017.01)
*A61K 9/00* (2006.01)
(Continued)

(52) U.S. Cl.
CPC .......... *A61K 47/554* (2017.08); *A61K 9/0053* (2013.01); *A61K 9/113* (2013.01);
(Continued)

(58) Field of Classification Search
CPC .... A61K 31/519; A61K 47/10; A61K 47/554; A61K 31/575
See application file for complete search history.

(56) References Cited

U.S. PATENT DOCUMENTS

2008/0026077 A1* 1/2008 Hilfinger ................ C07K 14/00
514/159

FOREIGN PATENT DOCUMENTS

JP   2008500387 A   1/2008
JP   2009514874 A   4/2009
(Continued)

OTHER PUBLICATIONS

Pangeni et al.; "Enhanced oral absorption of pemetrexed by ion-pairing complex formation with deoxycholic acid derivative and multiple nanoemulsion formulations: preparation, characterization, and in vivo oral bioavailability and antican"; Jun. 6, 2018; International Journal of Nanomedicine 13:3329-3351 (Year: 2018).*
(Continued)

*Primary Examiner* — Timothy P Thomas
(74) *Attorney, Agent, or Firm* — Westman, Champlin & Koehler, P.A.; Amanda M. Prose

(57) ABSTRACT

The present invention relates to an oral pharmaceutical composition containing pemetrexed as a water-soluble anticancer drug and a method of manufacturing the same, and more particularly to an oral pharmaceutical composition, in which an ion-binding complex of pemetrexed and a bile acid derivative as an oral absorption enhancer is formed, mixed with a pharmaceutical additive, and then provided in the form of a capsule or a tablet through pressing or included in
(Continued)

the internal water phase of a w/o/w (water-in-oil-in-water) multiple nanoemulsion, thus increasing the oral bioavailability of pemetrexed as the water-soluble anticancer drug, whereby pemetrexed, which is currently administered only in the form of an injection formulation, can be manufactured into a formulation capable of being orally administered, ultimately alleviating inconvenience and problems with use of injection formulations, improving patient compliance and contributing to a reduction in medical expenses.

2 Claims, 2 Drawing Sheets

(51) Int. Cl.
| | |
|---|---|
| A61K 31/519 | (2006.01) |
| A61K 47/10 | (2017.01) |
| A61K 9/113 | (2006.01) |
| A61K 9/20 | (2006.01) |
| A61K 9/48 | (2006.01) |
| A61K 31/353 | (2006.01) |
| A61K 31/513 | (2006.01) |
| A61K 31/575 | (2006.01) |
| A61K 47/26 | (2006.01) |
| A61K 47/40 | (2006.01) |
| A61K 47/44 | (2017.01) |

(52) U.S. Cl.
CPC .......... *A61K 9/2095* (2013.01); *A61K 9/4833* (2013.01); *A61K 31/353* (2013.01); *A61K 31/513* (2013.01); *A61K 31/519* (2013.01); *A61K 31/575* (2013.01); *A61K 47/10* (2013.01); *A61K 47/26* (2013.01); *A61K 47/40* (2013.01); *A61K 47/44* (2013.01)

(56) References Cited

FOREIGN PATENT DOCUMENTS

| | | |
|---|---|---|
| KR | 10-1260636 B1 | 5/2013 |
| KR | 10-2015-0020266 A | 2/2015 |
| WO | 2008/083107 A2 | 7/2008 |
| WO | 2016/178224 A1 | 11/2016 |

OTHER PUBLICATIONS

Mahmud et al.; "Oral pemetrexed facilitates low-dose metronomic therapy and enhances antitumor efficacy in lung cancer"; Jun. 13, 2018; Journal of Controlled Release; 284: 160-170; https://doi.org/10.1016/j.jconrel.2018.06.018 (Year: 2018).*

Pangeni et al.; "Enhanced oral absorption of pemetrexed by ion-pairing complex formation with deoxycholic acid derivative and multiple nanoemulsion formulations: preparation, characterization, and in vivo oral bioavailability and anticancer"; 2016; International Journal of Nanomedicine; 11:6379-6399 (Year: 2016).*

Hofmann et al.; "Bile salts of vertebrates: structural variation and possible evolutionary significance"; 2010; Journal of Lipid Research; 51:226-246 (Year: 2010).*

Pangeni et al.; "Enhanced oral absorption of pemetrexed by ion-pairing complex formation with deoxycholic acid derivative and multiple nanoemulsion formulations: preparation, characterization, and in vivo oral bioavailability and . . . "; 2016; International Journal of Nanomedicine; 11: 6379-6399 (Year: 2016).*

Jeon et al.; "Oral delivery of zoledronic acid by non-covalent conjugation with lysine-deoxycholic acid: In vitro characterization and in vivo anti-osteoporotic efficacy in ovariectomized rats"; 2015; European Journal of Pharmaceutical Sciences; 82(2016): 1-10 (Year: 2015).*

Park et al.; "Enhanced Oral Absorption of Ibandronate via Complex Formation with Bile Acid Derivative"; 2012; J. Pharm. Sci.; 102: 341-346, 2013 (Year: 2012).*

Lee, S. et al., "A new drug carrier, Nα-deoxycholyl-L-lysyl-methylester, for enhancing insulin absorption in the intestine" Diabetologia (2005) 48: 405-411.

Pangeni, R., et al. "Multiple nanoemulsion system for an oral combinational delivery of oxaliplatin and 5-fluorouracil: preparation and in vivo evaluation" International Journal of Nanomedicine (2016) 11: 6379-6399.

International Search Report issued for PCT/KR2018/011885, dated Apr. 24, 2019.

Written Opinion of the International Searching Authority issued for PCT/KR2018/011885, dated Apr. 24, 2019.

Jeon, O. et al. "Oral delivery of zoledronic acid by non-covalent conjugation with lysine-deoxycholic acid: In vitro characterization and in vivo anti-osteoporotic efficacy in ovariectomized rats" Eur J Pharm Sci. Jan. 20, 2016;82:1-10.

Park, J. W. et al. "Enhanced Oral Absorption of Ibandronate via Complex Formation with Bile Acid Derivative" J Pharm Sci. Feb. 2013;102(2):341-346.

Mahmud, F., et al. "Oral pemetrexed facilitates low-dose metronomic therapy and enhances antitumor efficacy in lung cancer" Journal of Controlled Release 284 (2018) 160-170.

Pangeni, R., et al. "Enhanced oral absorption of pemetrexed by ion-pairing complex formation with deoxycholic acid derivative and multiple nanoemulsion formulations: preparation, characterization, and in vivo oral bioavailability and anticancer effect" International Journal of Nanomedicine 2018:13, 3329-3351.

Extended European Search Report issued in corresponding EP patent application serial No. 18888126.2, dated Jul. 20, 2021.

Japanese Office Action issued in corresponding JP patent application serial No. 2020-545022, dated Jun. 8, 2021, with English Machine Translation.

Jeon, O. K. et al. "Oral delivery of zoledronic acid by non-covalent conjugation with lysine-deoxycholic acid: In vitro characterization and in vivo anti-osteoporotic efficacy in ovariectomized rats" Eur J Pharm Sci (2016) 82:1-10.

Park, J. W. et al. Enhanced oral absorption of ibandronate via complex formation with bile acid derivative J Pharm Sci (2013) 102(2):341-346.

Office Action issued for related Japanese patent application serial No. 2020-545022, dated Jan. 18, 2022, with English machine translation.

* cited by examiner

ORAL PHARMACEUTICAL COMPOSITION CONTAINING PEMETREXED AND PRODUCTION METHOD THEREOF

CROSS-REFERENCE TO RELATED APPLICATION

This application claims the priority benefit of Korean Patent Application No. 10-2017-0171384, filed on Dec. 13, 2017 in the Korean Intellectual Property Office, the disclosure of which is incorporated herein by reference.

TECHNICAL FIELD

The present invention relates to an oral pharmaceutical composition comprising an ion-binding complex of pemetrexed, as a water-soluble active material, and a bile acid derivative, as an oral absorption enhancer, and a method of manufacturing the same.

[Indication of Project Supporting the Present Invention]
[Project Identification No.] 52833722
[Government Department Name] Korea Ministry of SMEs and Startups
[Research Management Specialized Organization] Korea Agency for technical know-how of small and medium-sized businesses
[Research Project Name] Project for supporting business start-up growth and technical development
[Research Task Name] Development of activation enhancement drugs of immunosuppressant using oral metronomic anticancer drug
[Execution Organization] ICURE BNP CO., LTD.

BACKGROUND ART

Pemetrexed (PMX) is known to target thymidylate synthase (TS) and dihydrofolate reductase (DHFR) by entering cells through a reduced folate carrier (RFC), which is the main intracellular transport pathway of folic acid, followed by activation in the form of a polyglutamate derivative by folylpolyglutamate synthetase (FPGS).

Currently, pemetrexed is developed under the trade name Alimta® and is commercially available as a therapeutic agent for malignant pleural mesothelioma and as a therapeutic agent for non-small-cell lung cancer. Alimta® is commercially available in the dosage form of a lyophilized formulation that must be reconstituted before administration, specifically a lyophilized powder (100 mg or 500 mg) that must be reconstituted with a 0.9% sodium chloride solution when administered to a patient and finally diluted (final concentration: 0.25 mg/ml) with a 0.9% sodium chloride solution.

Pemetrexed is currently administered to patients only in the form of an injection formulation, and a lyophilized formulation thereof has to be used after dilution with water for injection, with a glucose solution, or with a 0.9% sodium chloride solution immediately before administration to patients. However, the lyophilization process is complicated and the manufacturing cost is high, and moreover, reconstitution is required in order to use the lyophilized product. However, during the reconstitution process, problems such as loss of pemetrexed, precipitation, generation of undesirable particles during reconstitution, and risk of exposure to contamination may occur. In particular, the problem of contamination is very serious due to the toxicity of antitumor substances.

Recently, anticancer therapy through oral administration is receiving attention because it may minimize the inconvenience in which a patient is receiving injections after visit to the hospital and may be performed at home, and may thus improve the patient's convenience in receiving treatment and quality of life. Moreover, it is possible to realize long-term exposure of anticancer drugs to cancer cells at low concentration by maintaining the drug concentration in the blood for a long period of time, thus retaining drug efficacy and minimizing side effects, thereby facilitating the application of anticancer drugs as a preventive chronic therapy for preventing the recurrence and metastasis of cancer.

However, oral delivery of anticancer drugs has many limitations due to the physicochemical properties and physiological disorders of the active ingredient. These barriers include metabolic processes before systemic blood transfer of drugs, drug instability in the gastrointestinal tract, low solubility, low intestinal membrane permeability, and excretion by p-glycoprotein (p-gp).

In particular, pemetrexed faces obstacles to use in oral formulations because it exhibits low oral bioavailability due to the low intestinal membrane permeability thereof. Thorough research into compositions having improved stability for parenteral administration of pemetrexed have been carried out, but technology for oral dosage forms containing pemetrexed, which is the water-soluble active material, has yet to be developed.

Therefore, the present inventors studied the production of a water-soluble active material such as pemetrexed into a formulation for oral administration, and have developed a method in which pemetrexed in a solution including a dispersant is formed into an ion-binding complex with a bile acid derivative, functioning as an oral absorption enhancer, and the ion-binding complex is mixed with a pharmaceutical additive, granulated, and then filled in a capsule, pressed into a tablet or included in the internal water phase of a w/o/w (water-in-oil-in-water) multiple nanoemulsion, thereby manufacturing a formulation for oral administration having increased intestinal membrane permeability of the drug, thus culminating in the present invention.

As documents related to the present invention, reference is to be made to Patent Documents KR1020150020266 A and KR101260636 B1.

DISCLOSURE

Technical Problem

Accordingly, an objective of the present invention is to provide an oral pharmaceutical composition containing pemetrexed and a method of manufacturing the same, in which pemetrexed, as a water-soluble anticancer drug, is formed into an ion-binding complex with a bile acid derivative, as an oral absorption enhancer, and then granulated or included in the internal water phase of a w/o/w (water-in-oil-in-water) multiple nanoemulsion, thereby manufacturing a formulation for oral administration having increased intestinal membrane permeability of the drug, thus alleviating inconvenience and problems with use of injection formulations, improving patient compliance and contributing to a reduction in medical expenses.

Technical Solution

In order to accomplish the above objective, the present invention provides a formulation composition for oral administration of pemetrexed comprising pemetrexed and a bile acid derivative.

According to the present invention, the oral formulation containing pemetrexed may be configured such that a mixture of pemetrexed or a pharmaceutically acceptable salt thereof and a dispersant is formed into an ion-binding complex with a bile acid derivative as an oral absorption enhancer in order to improve the lipophilicity of the drug and to promote the diffusion of the bound drug through interaction with a bile acid transporter present on the surface of the intestinal membrane, and the ion-binding complex is mixed with a pharmaceutically usable additive, granulated, and pressed into a tablet or filled in a hard capsule.

The bile acid derivative may be W-deoxycholyl-L-lysyl-methylester (DCK), and may be used in an amount of 0.5 to 5 moles based on 1 mole of pemetrexed.

The dispersant is not particularly limited, and may be independently at least one selected from the group consisting of poloxamer, polyvinylpyrrolidone, caprylocaproyl macrogol-8 glyceride (Labrasol™), Cremophor™, glycerol monocaprylocaprate (™ MCM), lauroyl macrogol-32 glyceride (Gelucire™ 44/14), Solutrol®, polysorbate (Tween), sorbitan monolaurate (Span), mannitol, sucrose, lactose, glucose, trehalose, glycerol, fructose, maltose, dextran, cyclodextrin, glycine, alanine, and lysine.

The oral formulation of the present invention may further include a pharmaceutical additive, such as a diluent, a binder, a swelling agent, a lubricant, etc.

The diluent is not particularly limited, and examples thereof may include lactose, dextrin, mannitol, sorbitol, starch, microcrystalline cellulose, calcium hydrogen phosphate, anhydrous calcium hydrogen phosphate, calcium carbonate, saccharides, and the like.

The binder is not particularly limited, and examples thereof may include polyvinylpyrrolidone, copovidone, gelatin, starch, sucrose, methyl cellulose, ethyl cellulose, hydroxyethyl cellulose, hydroxypropyl cellulose, hydroxypropyl alkyl cellulose, and the like.

The swelling agent may include at least one component selected from the group consisting of crosslinked polyvinylpyrrolidone, crosslinked sodium carboxymethyl cellulose, crosslinked calcium carboxymethyl cellulose, crosslinked carboxymethyl cellulose, sodium starch glycolate, carboxymethyl starch, sodium carboxymethyl starch, potassium methacrylate-divinylbenzene copolymer, amylose, crosslinked amylose, starch derivatives, microcrystalline cellulose and cellulose derivatives, and cyclodextrin and dextrin derivatives.

The lubricant is not particularly limited, and examples thereof may include stearic acid, stearate, talc, corn starch, carnauba wax, light anhydrous silicic acid, magnesium silicate, synthetic aluminum silicate, hardened oil, white wax, titanium oxide, microcrystalline cellulose, macrogol 4000 and 6000, isopropyl myristate, calcium hydrogen phosphate, and the like.

In addition, the oral formulation containing pemetrexed according to the present invention may be manufactured by (a) forming an ion-binding complex by adding positively charged bile acid derivative to mixture of pemetrexed and a dispersant, (b) adding a primary surfactant and a primary auxiliary surfactant to the ion-binding complex solution, (c) preparing a water-in-oil (w/o) primary nanoemulsion by dispersing the mixture obtained in step (b) in a primary oil phase, and (d) preparing a water-in-oil-in-water (w/o/w) secondary nanoemulsion filled in a capsule by adding the w/o primary nanoemulsion with a mixture of a secondary surfactant and a secondary auxiliary surfactant.

The bile acid derivative may be W-deoxycholyl-L-lysyl-methylester (DCK), and may be used in an amount of 0.5 to 5 moles based on 1 mole of pemetrexed.

The primary oil phase may be at least one selected from the group consisting of silicone oil, ester oil, hydrocarbon oil, propylene glycol monocaprylate (Capryol® 90), propylene glycol dicaprylocaprate (Labrafac PG), oleoyl macrogol-6 glyceride (Labrafil® M1944 CS), lauroyl macrogol-6 glyceride (Labrafil® M2130 CS), linoleoyl macrogol-6 glyceride (Labrafil® M2125 CS), heavy-chain triglyceride (Labrafac), oleic acid, stearic acid, glyceryl behenate (Compritol® 888), glycerol monostearate, and castor oil.

The amount of the primary oil phase in the w/o/w secondary nanoemulsion may be 0.1 to 40 wt % based on the total weight of the composition.

Each of the primary and secondary surfactants may independently be at least one selected from the group consisting of poloxamer, caprylocaproyl macrogol-8 glyceride (Labrasol™), Cremophor™, glycerol monocaprylocaprate (Capmul™ MCM), lauroyl macrogol-32 glyceride (Gelucire™ 44/14), Solutrol®, polysorbate (Tween), and sorbitan monolaurate (Span).

Each of the primary and secondary auxiliary surfactants may independently be at least one selected from the group consisting of diethylene glycol monoethyl ether (Transcutol HP), polysorbate, polyethylene glycol, butylene glycol, propylene glycol, ethanol, and isopropanol.

The amount of the mixture of the primary surfactant and the primary auxiliary surfactant and the mixture of the secondary surfactant and the secondary auxiliary surfactant may be 0.1 to 40 wt % based on the total weight of the composition.

The primary auxiliary surfactant and the secondary auxiliary surfactant may be independently mixed at a weight ratio of 1:0.1 to 1:10 relative to the primary surfactant and the secondary surfactant, respectively.

In step (a), a dispersant selected from among monosaccharides, polysaccharides, dietary fiber, gums, surfactants and proteins may be further included, and the dispersant may be used in an amount of 0.1 to 100 parts by weight based on 1 part by weight of pemetrexed.

The w/o primary nanoemulsion may further include, in the internal water phase thereof, a hydrophilic active ingredient selected from among 5-fluorouracil (5-FU) and leucovorin.

In step (d), the w/o/w secondary nanoemulsion may further include, in the primary oil phase thereof, a fat-soluble active ingredient selected from among a poorly soluble anticancer drug, curcumin, quercetin, a natural extract containing curcumin or quercetin as an active ingredient, and mixtures thereof.

In addition, the present invention provides an oral pharmaceutical composition containing pemetrexed manufactured by the above method.

Advantageous Effects

According to the present invention, an oral pharmaceutical composition containing pemetrexed can be configured such that an ion-binding complex of pemetrexed as a water-soluble anticancer drug and a bile acid derivative as an oral absorption enhancer is formed and loaded in a w/o/w multiple nanoemulsion, thus making it possible to manufacture a formulation capable of being orally administered due to increased oral bioavailability, thereby alleviating inconvenience and problems with use of existing injection formulations, improving patient compliance and contributing to a reduction in medical expenses.

MODE FOR INVENTION

Figure 1:
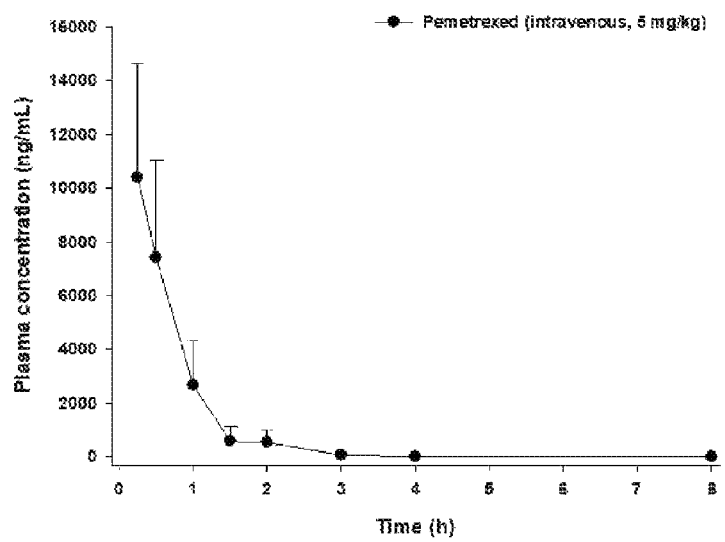
FIG. 1 shows the blood drug concentration over time after intravenous injection of 5 mg/kg pemetrexed into rats.

Hereinafter, a detailed description will be given of an oral pharmaceutical composition containing pemetrexed according to the present invention and a method of manufacturing the same.

According to the present invention, the method of manufacturing an oral pharmaceutical granular composition containing pemetrexed comprising (a) dissolving pemetrexed in a solution including a dispersant, (b) forming an ion-binding complex by adding a positively charged bile acid derivative to the pemetrexed solution, (c) drying the ion-binding complex solution, (d) preparing granules by mixing the dried product with a binder and a diluent as pharmaceutical additives, and (e) adding the granules with a lubricant and filling the granules in a capsule or pressing the granules into a tablet.

In addition, the method of manufacturing an oral pharmaceutical emulsion composition containing pemetrexed according to the present invention comprising (a) forming an ion-binding complex by adding a positively charged bile acid derivative to pemetrexed and a dispersant in a solution, (b) adding a primary surfactant and a primary auxiliary surfactant to the ion-binding complex solution, (c) preparing a water-in-oil (w/o) primary nanoemulsion by dispersing the mixture obtained in step (b) in a primary oil phase, and (d) preparing a water-in-oil-in-water (w/o/w) secondary nanoemulsion by adding the w/o primary nanoemulsion with a mixture of a secondary surfactant and a secondary auxiliary surfactant.

Here, pemetrexed is a hydrophilic and negatively charged active material, and the pemetrexed aqueous solution is added with a bile acid derivative, which is a positively charged oral absorption enhancer, thus forming an ion-binding complex.

The bile acid derivative is an amphiphilic material having a positive charge in an aqueous solution, and is preferably $N^{\alpha}$-deoxycholyl-L-lysyl-methylester (DCK) resulting from chemical bonding of L-lysine and deoxycholic acid. Moreover, it is preferably included in an amount of 0.5 to 5 moles, and more preferably 1 to 2 moles, based on 1 mole of pemetrexed.

The DCK functions as an oral absorption enhancer, and is positively charged in an aqueous solution to form an ion-binding complex with the negatively charged hydrophilic active ingredient, thus increasing the lipophilicity of the hydrophilic drug molecule to thereby enhance the distribution thereof into the oil phase. Deoxycholic acid is an amphiphilic molecule composed of a hydrophobic α portion and a hydrophilic β portion, and is capable of increasing the membrane permeability of the drug by increasing the flexibility of the intestinal cell membrane and the solubility of the fat-soluble drug in the membrane by vertically binding to the membrane surface of the cell lipid bilayer and disturbing the acyl chain of the lipid matrix. Moreover, deoxycholic acid, which is a bile acid derivative coupled with the drug, may be recognized by a bile acid reabsorption transporter present on the surface of the intestinal membrane, which forms a high concentration gradient of the drug on the surface of the intestinal mucosa, thus accelerating the diffusion of the drug to the intestinal membrane. Therefore, the absorption enhancement effect due to the selective interaction of the ion-binding complex of the drug and the absorption enhancer with the bile acid reabsorption transporter may minimize the decrease in the action of the absorption enhancer diluted by the fluid present in the gastrointestinal tract after administration, making it possible to increase the gastrointestinal absorption rate of the hydrophilic drug even upon minimal use thereof, unlike conventional absorption enhancers that are simply added through physical mixing.

In order to prepare the ion-binding complex formed in an aqueous solution phase into a solid powder phase, it may be additionally dried through hot-air drying, freeze-drying, spray drying, or the like. Moreover, a dispersant may be further added in the formation of the ion-binding complex in order to realize rapid redispersion in the aqueous solution of the ion-binding complex in a dry powder form.

The dispersant may be selected from among monosaccharides, polysaccharides, dietary fiber, gums, surfactants and proteins, and is preferably selected from among poloxamer, polyvinylpyrrolidone, caprylocaproyl macrogol-8 glyceride (Labrasol™), Cremophor™, glycerol monocaprylocaprate (Capmul™ MCM), lauroyl macrogol-32 glyceride (Gelucire™ 44/14), Solutrol®, polysorbate (Tween), sorbitan monolaurate (Span), mannitol, sucrose, lactose, glucose, trehalose, glycerol, fructose, maltose, dextran, cyclodextrin, glycine, alanine, and lysine, and is more preferably selected from among poloxamer, polyvinylpyrrolidone, caprylocaproyl macrogol-8 glyceride (Labrasol™), cyclodextrin, lactose, and mannitol.

The dispersant is preferably included in an amount of 0.1 to 100 parts by weight, and more preferably 0.1 to 60 parts by weight, based on 1 part by weight of pemetrexed.

The w/o primary nanoemulsion may further include, in the internal water phase thereof, a hydrophilic active ingredient that may exhibit an anticancer synergistic effect in combination with the ion-binding complex, and the hydrophilic active ingredient may be selected from among 5-fluorouracil (5-FU) and leucovorin. By incorporating the hydrophilic active ingredient into the nanoemulsion formulation, it is possible to improve oral bioavailability by enhancing the gastrointestinal absorption rate of the drug.

The primary oil phase used in the preparation of the w/o primary nanoemulsion is preferably at least one selected from the group consisting of silicone oil, ester oil, hydrocarbon oil, propylene glycol monocaprylate (Capryol® 90), propylene glycol dicaprylocaprate (Labrafac PG), oleoyl macrogol-6 glyceride (Labrafil® M1944 CS), lauroyl macrogol-6 glyceride (Labrafil® M2130 CS), linoleoyl macrogol-6 glyceride (Labrafil® M2125 CS), heavy-chain triglyceride (Labrafac), oleic acid, stearic acid, glyceryl behenate (Compritol® 888), glycerol monostearate, and castor oil.

The amount of the primary oil phase in the w/o/w secondary nanoemulsion is preferably 0.1 to 40 wt %, and more preferably 1 to 20 wt %, based on the total weight of the composition. If the amount of the oil phase is less than 1 wt % or exceeds 20 wt %, the particles of the emulsion may be enlarged, thus deteriorating emulsion stability. Here, the amount of the oil phase means the total amount of the oil phase relative to the total weight of the w/o/w secondary nanoemulsion including the secondary external water phase, but not including an emulsion stabilizer.

The w/o/w secondary nanoemulsion in step (d) may further include, in the primary oil phase thereof, a fat-soluble active ingredient capable of improving the pharmacological therapeutic efficacy of the ion-binding complex, and the fat-soluble active ingredient may be a poorly soluble anticancer agent such as paclitaxel, docetaxel or doxorubicin, curcumin, quercetin, a natural extract containing curcumin or quercetin as an active ingredient, or mixtures thereof. The fat-soluble active ingredient is included in the oil phase of the nanoemulsion formulation, thus solubilizing the active ingredient to thereby increase the gastrointestinal absorption rate thereof, ultimately improving oral bioavailability and pharmacological activity.

The primary and secondary surfactants allow the internal water phase in which the ion-binding complex is dispersed to be dispersed in the oil phase and also allow the w/o primary nanoemulsion to be dispersed well in the external water phase of the w/o/w secondary nanoemulsion. It is preferred that each of the primary and secondary surfactants independently be at least one selected from the group consisting of poloxamer, caprylocaproyl macrogol-8 glyceride (Labrasol™), Cremophor™, glycerol monocaprylocaprate (Capmul MCM), lauroyl macrogol-32 glyceride (Gelucire™ 44/14), Solutrol®, polysorbate (Tween), and sorbitan monolaurate (Span).

The primary and secondary auxiliary surfactants serve to reduce the surface energy so that the internal water phase in which the ion-binding complex is dispersed may be dispersed in the oil phase by the surfactant, and also allow the w/o primary nanoemulsion to be dispersed well in the external water phase of the w/o/w secondary nanoemulsion by the surfactant. It is preferred that each of the primary and secondary auxiliary surfactants independently be at least one selected from the group consisting of diethylene glycol monoethyl ether (Transcutol HP), polysorbate, polyethylene glycol, butylene glycol, propylene glycol, ethanol, and isopropanol.

The amount of the mixture of the primary surfactant and the primary auxiliary surfactant and the mixture of the secondary surfactant and the secondary auxiliary surfactant is preferably 0.1 to 40 wt %, and more preferably 1 to 20 wt %, based on the total weight of the composition. If the amount thereof is less than 1 wt % or exceeds 20 wt %, the stability of the emulsion may decrease. Here, the amount of the mixture of the primary surfactant and the primary auxiliary surfactant and the mixture of the secondary surfactant and the secondary auxiliary surfactant means the total amount of the primary and secondary surfactants and the primary and secondary auxiliary surfactants relative to the total weight of the w/o/w secondary nanoemulsion including the secondary external water phase.

Moreover, the primary auxiliary surfactant and the secondary auxiliary surfactant are mixed with the primary surfactant and the secondary surfactant, respectively, and are each independently mixed at a weight ratio of preferably 1:0.1 to 1:10, and more preferably 1:0.5 to 1:2, relative to the primary surfactant and the secondary surfactant, respectively.

In addition, the present invention pertains to an oral pharmaceutical composition containing pemetrexed manufactured by the above method.

As a drug transporter of the ion-binding complex of pemetrexed and bile acid derivative according to the present invention, a w/o/w multiple nanoemulsion form may be used. The oil phase in this system protects the ion-binding complex in the gastrointestinal tract, minimizes the dilution effect of the absorption enhancer, and enables high dispersibility of the amphipathic ion-binding complex in the gastrointestinal tract after administration. Moreover, the multiple nanoemulsion is known to enhance the absorption of the drug by modifying the structure and fluidity of the intestinal membrane in the gastrointestinal tract. In particular, when 5-fluorouracil, which is a hydrophilic drug that cannot be ionically complexed with a bile acid derivative, is also loaded in the internal water phase, the intestinal membrane permeability and oral bioavailability of the drug may be improved by the multiple nanoemulsion.

Moreover, Labrasol™ and Cremophor™ EL, which are surfactants used for multiple nanoemulsion, may be used to disperse the primary internal water phase in the oil phase or to disperse the w/o primary nanoemulsion in the external water phase of the w/o/w secondary nanoemulsion. Labrasol™ is known to interact with F-actin (filamentous actin) and ZO-1 (zonula occludens-1) to disassemble tight junctions between small intestinal epithelial cells, and in the case of Cremophor™ EL, it was confirmed that it is possible to promote absorption by increasing the fluidity of the cell membrane and loosening tight junctions. Therefore, the membrane permeability of the hydrophilic active ingredient, 5-FU, may be increased through the intercellular path by the application of a surfactant that induces a decrease in binding between small intestinal epithelial cells. Moreover, Cremophor™ EL may bind to the hydrophobic region of P-gp, which results in a change in the shape of P-gp, thus reducing the drug's release into the intestinal tract, thereby increasing the limited gastrointestinal absorption rate of the P-gp-mediated drug, like 5-FU.

A better understanding of the present invention will be given through the following examples. However, these examples are set forth to illustrate the present invention, and are not to be construed as limiting the scope of the present invention.

Example 1: Preparation of Bile Acid Derivative

As an oral absorption enhancer, a bile acid derivative was prepared by chemically binding positively charged lysine to deoxycholic acid.

2.6 g of deoxycholic acid was dissolved in a mixture of 6.4 ml of ethyl chloroformate, 7.4 ml of N-methylmorpholine and 800 ml of tetrahydrofuran (THF), added with a solution of 2.7% (w/v) H-Lys(Boc)-OMeHCl in N-methylmorpholine, and then refluxed for 2 hr. After stirring at room temperature overnight, the resulting precipitate was filtered and dried by evaporating the solvent. The precipitate thus obtained was passed through a column using a mixture of chloroform and methanol to separate Lys(Boc)DOCA. The Lys(Boc)DOCA thus obtained was dissolved again in a mixture of ethyl chloride and methanol in an ice bath, the solvent was thoroughly removed, and the resulting residue was dissolved in purified water and then washed with chloroform. The aqueous solution layer was recovered and then lyophilized, thereby obtaining a deoxycholic acid-lysine derivative (DCK) in a powder form.

Example 2: Preparation of PMX/DCK Ion-Binding Complex

An ion-binding complex was formed by dissolving pemetrexed (PMX) in purified water and slowly adding a DCK aqueous solution with stirring so that the molar ratio of pemetrexed to DCK was 1:1. The mixed solution thus obtained was centrifuged and then lyophilized, thereby preparing a PMX/DCK ion-binding complex in a powder form.

Example 3: Preparation of Tablet and Capsule Including PMX/DCK Ion-Binding Complex 500 mg of poloxamer and 375 mg of Labrasol™ were dissolved in 10 ml of purified water and then 50 mg of pemetrexed was added thereto and dissolved therein. Separately, 66.825 mg of DCK was dissolved in 10 ml of purified water, after which the DCK aqueous solution was slowly added to the pemetrexed solution with stirring so that the molar ratio of pemetrexed to DCK was 1:1, thus forming an ion-binding complex. The mixed solution thus prepared was lyophilized to afford a dispersant-added PMX/DCK ion-binding complex in a powder form. Here, poloxamer and Labrasol™ were used as dispersants. 198.364 mg of the dispersant-added PMX/DCK ion-binding complex was added with 30 mg of copovidone, 30 mg of microcrystalline cellulose and 38.636 mg of lactose, mixed, added with 3 mg of magnesium stearate, further mixed, and then pressed into an appropriate form to yield a tablet, or filled into a capsule.

Example 4: Preparation of PMX/DCK Ion-Binding Complex

Pemetrexed was dissolved in purified water, added with a hydroxypropyl beta-cyclodextrin (HP-beta CD) aqueous solution at a molar ratio of 1:1 with pemetrexed, and stirred overnight. Thereafter, poloxamer 188 was added at the same weight ratio as pemetrexed and stirred, after which a DCK aqueous solution was slowly added thereto with stirring so that the molar ratio of pemetrexed to DCK was 1:1, thus forming a PMX/DCK ion-binding complex. The mixed solution thus obtained was lyophilized to afford a dispersant-added PMX/DCK ion-binding complex in a powder form. Here, hydroxypropyl beta-cyclodextrin and poloxamer 188 were used as dispersants.

Example 5: Preparation of w/o/w Nanoemulsion Including PMX/DCK Ion-Binding Complex 108.82 mg of the lyophilized powder mixture of the PMX/DCK ion-binding complex and the dispersants (hydroxypropyl beta-cyclodextrin and poloxamer) was redispersed in purified water, and was then added with 100 mg of a 1:2 primary-surfactant/primary-auxiliary-surfactant mixture (Labrasol™ Transcutol HP=1:2 (w/w)). As a primary oil phase, 57.2 mg of Capryol® 90 was added and mixed, thus preparing a primary w/o nanoemulsion. The primary w/o nanoemulsion was added with 600 mg of a 1:2 secondary-surfactant/secondary-auxiliary-surfactant mixture (Cremophor™ EL:Transcutol HP=1:1 (w/w)), mixed, and dispersed in 1200 mg of purified water, thereby preparing a w/o/w secondary nanoemulsion.

Example 6: Preparation of w/o/w Nanoemulsion Including PMX/DCK Ion-Binding Complex and Quercetin The mixture of 66.02 mg of the PMX/DCK ion-binding complex (corresponding to 10 mg of pemetrexed) and the dispersants (hydroxypropyl beta-cyclodextrin and poloxamer) was redispersed in 38 mg of purified water and then added with 112 mg of a 1:1 primary-surfactant/primary-auxiliary-surfactant mixture (Labrasol™:Tween 80=1:1, w/w). As a primary oil phase, 50 mg of Labrafil® M1944 was added and mixed, thereby preparing a primary w/o nanoemulsion.

The primary w/o nanoemulsion was added with 20 mg of quercetin and 630 mg of a secondary-surfactant/secondary-auxiliary-surfactant mixture (Tween 80:Cremophor™ EL:PEG 400=1:2:2, w/w/w), mixed, and then dispersed in 800 mg of purified water, thereby preparing a w/o/w secondary nanoemulsion.

Example 7: Measurement of Artificial Intestinal Membrane Permeability of Oral Composition Including PMX/DCK Ion-Binding Complex The intestinal membrane permeability of pemetrexed (PMX), the mixture of hydroxypropyl beta-cyclodextrin and pemetrexed (HP-beta CD/PMX), the mixture of hydroxypropyl beta-cyclodextrin and PMX/DCK ion-binding complex (HP-beta CD/PMX/DCK), the mixture of hydroxypropyl beta-cyclodextrin, PMX/DCK ion-binding complex and poloxamer (HP-beta CD/PMX/DCK/P188) prepared in Example 4, and the w/o/w nanoemulsion including the mixture of hydroxypropyl beta-cyclodextrin, PMX/DCK ion-binding complex and poloxamer (HP-beta CD/PMX/DCK/P188) prepared in Example 5 was evaluated using an artificial intestinal membrane (PAMPA; BD Biosciences, San Jose, Calif., USA). The results thereof are shown in Table 1 below.

Each sample was diluted with phosphate-buffered saline (PBS, pH 6.8) so that the concentration of pemetrexed was 200 μg/ml, and was then added in an amount of 200 μl to the donor compartment of each well of a PAMPA plate, each acceptor compartment thereof was added with 300 μl of phosphate-buffered saline (PBS, pH 6.8), and the donor compartment and the acceptor compartment were linked and then allowed to stand at room temperature for 5 hr, after which the sample was recovered from the donor compartment and the acceptor compartment of each well of the PAMPA plate and the concentration of the permeated drug was measured as follows.

The concentrations of PMX and PMX/DCK were analyzed by introducing 20 μl of the sample into an HPLC system with a C18 column (4.6×250 mm, 5 μm, 100 □) and allowing a mixture of purified water (pH 3.2, adjusted with phosphoric acid) and acetonitrile at 80:20 (v/v) as a mobile phase to flow at a flow rate of 1.0 ml/min. The detection of PMX and PMX/DCK was performed at 254 nm.

The effective permeability ($P_e$) of each drug was calculated using the following equation.

$$P_e = -\ln[1 - C_A(t)/C_{equilibrium}]/[A \times (1/V_D + 1/V_A) \times t]$$

($P_e$: permeability (cm/s); A: effective filter area (f×0.3 cm$^2$; f: pores on surface of filter (f=0.76)); $V_D$: volume of donor compartment (0.2 ml); $V_A$: volume of acceptor compartment (0.3 ml); t: permeation time (sec); $C_A(t)$: drug concentration in acceptor compartment at time t; $C_{equilibrium}$:

$[C_D(t) \times V_D + C_A(t) \times V_A]/(V_D+V_A)$; $C_D(t)$: residual drug concentration of donor compartment at time t)

TABLE 1

| Sample | Permeability ($\times 10^{-6}$, cm/s) |
|---|---|
| PMX | 3.73 ± 1.15 |
| HP-beta CD/PMX | 5.78 ± 1.37 |
| HP-beta CD/PMX/DCK | 14.0 ± 2.08 |
| HP-beta CD/PMX/DCK/P188 (Example 4) | 19.6 ± 1.27 |
| w/o/w nanoemulsion including HP-beta CD/PMX/DCK/P188 (Example 5) | 21.0 ± 3.27 |

As shown in Table 1, the artificial intestinal membrane permeability of pemetrexed was increased 3.75 times after formation of the ion-binding complex with DCK, and when the ion-binding complex was included in the w/o/w multiple nanoemulsion formulation, the artificial intestinal membrane permeability of pemetrexed was increased 5.63 times compared to pemetrexed alone.

Example 8: Measurement of Artificial Intestinal Membrane Permeability of w/o/w Nanoemulsion Including PMX/DCK Ion-Binding Complex and Quercetin The intestinal membrane permeability of pemetrexed (PMX), quercetin and the w/o/w secondary nanoemulsions including the mixture of hydroxypropyl beta-cyclodextrin, PMX/DCK ion-binding complex and poloxamer (HP-beta CD/PMX/DCK/P188) prepared in Example 5 and quercetin was evaluated using an artificial intestinal membrane (PAMPA; BD Biosciences, San Jose, Calif., USA). The results thereof are shown in Table 2 below.

Each sample was diluted with phosphate-buffered saline (PBS, pH 6.8) so that the concentration of pemetrexed was 200 μg/ml and the concentration of quercetin was 400 μg/ml, and was then added in an amount of 200 μl to the donor compartment of each well of a PAMPA plate, each acceptor compartment thereof was added with 300 μl of phosphate-buffered saline (PBS, pH 6.8), and the donor compartment and the acceptor compartment were linked and then allowed to stand at room temperature for 5 hr, after which the sample was recovered from the donor compartment and the acceptor compartment of each well of the PAMPA plate, and the concentration of the permeated drug was measured as follows.

The concentrations of PMX and PMX/DCK were analyzed by introducing 20 μl of the sample into an HPLC system with a C18 column (4.6×250 mm, 5 μm, 100 □) and allowing a mixture of purified water (pH 3.2, adjusted with phosphoric acid) and acetonitrile at 80:20 (v/v) as a mobile phase to flow at a flow rate of 1.0 ml/min. The detection of PMX and PMX/DCK was performed at 254 nm.

The concentration of quercetin was analyzed at 35° C. by introducing 20 μl of the sample into an HPLC system with a C18 column (4.6×150 mm, 5 μm, 100 □) and allowing a mixture of purified water (pH 2.6, adjusted with 2% acetic acid) and acetonitrile at 40:40 (v/v) as a mobile phase to flow at a flow rate of 1.0 ml/min. The UV detection was performed at 370 nm.

The effective permeability ($P_e$) of each drug was calculated in the same manner as in Example 7.

TABLE 2

| Sample | Permeability ($\times 10^{-6}$, cm/s) |
|---|---|
| PMX | 2.52 ± 0.60 |
| w/o/w nanoemulsion including HP-beta CD/PMX/DCK/P188 (Example 6) | 35.5 ± 5.89 |
| Quercetin | 4.51 ± 5.10 |
| w/o/w nanoemulsion including quercetin (Example 6) | 29.3 ± 1.88 |

As shown in Table 2, the artificial intestinal membrane permeability of pemetrexed from the w/o/w multiple nanoemulsion including the PMX/DCK ion-binding complex of Example 6 was increased 14.1 times compared to pemetrexed alone, and when quercetin was included in the w/o/w multiple nanoemulsion of Example 6, the artificial intestinal membrane permeability thereof was increased 6.50 times compared to quercetin alone due to the solubilization of quercetin.

Example 9: Measurement of Intestinal Cell Membrane Permeability of w/o/w Nanoemulsion Including PMX/DCK Ion-Binding Complex The intestinal cell membrane permeability of pemetrexed (PMX), the tablet or capsule composition including the PMX/DCK ion-binding complex prepared in Example 3, the mixture of hydroxypropyl beta-cyclodextrin and pemetrexed (HP-beta CD/PMX), the mixture of hydroxypropyl beta-cyclodextrin and PMX/DCK ion-binding complex (HP-beta CD/PMX/DCK), the mixture of hydroxypropyl beta-cyclodextrin, PMX/DCK ion-binding complex and poloxamer (HP-beta CD/PMX/DCK/P188) prepared in Example 4, and the w/o/w nanoemulsion including the mixture of hydroxypropyl beta-cyclodextrin, PMX/DCK ion-binding complex and poloxamer (HP-beta CD/PMX/DCK/P188) prepared in Example 5 was evaluated using a Caco-2 cell monolayer membrane. The results thereof are shown in Table 3 below.

Caco-2 cells were treated at $3 \times 10^5$ cells in each well of a 12-well Transwell (pore size: 0.4 μm, surface area: 1.12 cm$^2$; Corning, N.Y., USA). Dulbecco's modified Eagles medium (DMEM; Lonza, Basel, Switzerland) containing 10% fetal bovine serum (FBS; Gibco™, Thermo Fisher Scientific) and 1% penicillin/streptomycin (Gibco™) was replaced every 48 hr for 21 days to 29 days, and a Caco-2 cell membrane having a transepithelial electrical resistance (TEER) of 350 Ωcm$^2$ or more was used for in-vitro intestinal cell membrane permeability tests.

Specifically, the culture medium was removed, culture was performed at 37° C. for 20 min with 0.5 ml of a Hanks' balanced salt solution (HESS), HBSS was removed, and each sample was diluted with HBSS so that the concentration of pemetrexed was 200 μg/ml, after which each sample thus diluted was added in an amount of 0.5 ml to the apical compartment of the Transwell, and the basolateral compartment of the Transwell was added with 1.5 ml of HBSS, followed by culturing at 37° C. After sample treatment, 100 μl of the sample was collected from the basolateral compartment of each well at 0.5, 1, 2, 3, 4 and 5 hr and then filtered with a membrane filter, after which the concentrations of PMX and the PMX/DCK ion-binding complex that permeated the intestinal cell membrane were measured using the same HPLC system as in Example 7. Moreover, the apparent permeation coefficient ($P_{app}$) of PMX and the PMX/DCK ion-binding complex was calculated using the following equation.

$$P_{app} = dQ/dt \times 1/(A \times C_0)$$

(dQ/dt: weight of drug that permeated basolateral compartment per unit time (μmol/s), $C_0$: initial concentration of PMX or PMX/DCK ion-binding complex in apical compartment (μmol/l), A: permeation area (cm$^2$)).

TABLE 3

| Sample | Permeability (×10$^{-6}$, cm/s) |
| --- | --- |
| PMX | 0.50 ± 0.09 |
| Tablet and capsule composition including PMX/DCK (Example 3) | 21.3 ± 0.67 |
| HP-beta CD/PMX | 0.76 ± 0.19 |
| HP-beta CD/PMX/DCK | 1.15 ± 0.10 |
| HP-beta CD/PMX/DCK/P188 (Example 4) | 4.23 ± 0.46 |
| w/o/w nanoemulsion including HP-beta CD/PMX/DCK/P188 (Example 5) | 4.89 ± 0.13 |

As shown in Table 3, the Caco-2 intestinal cell membrane permeability of pemetrexed when prepared into a tablet or capsule composition after formation of the ion-binding complex with DCK was increased 42.6 times compared to pemetrexed alone. The Caco-2 intestinal cell membrane permeability after formation of the ion-binding complex of pemetrexed and DCK (HP-beta CD/PMX/DCK) was increased 2.30 times compared to pemetrexed alone, and when the ion-binding complex was included in the w/o/w multiple nanoemulsion formulation of Example 5, the Caco-2 intestinal cell membrane permeability thereof was increased 9.78 times compared to pemetrexed alone.

Example 10: Measurement of In-Vivo Bioavailability of Oral Pharmaceutical Composition Including PMX/DCK Ion-Binding Complex Each of pemetrexed and a tablet or capsule composition including the PMX/DCK ion-binding complex prepared in Example 3 was dissolved in distilled water and then orally administered in an amount of 500 μl into rats. Separately, in order to evaluate oral bioavailability, a solution of pemetrexed in distilled water was injected in an amount of 200 μl into rats through the tail vein thereof. Blood samples (200 μl) were collected at scheduled times after individual drug administrations and immediately mixed with 50 μl of a sodium citrate (3.8%) solution. The collected blood samples were centrifuged at 2,500×g and 4° C. for 15 min, pemetrexed in plasma was extracted using a solid-phase extraction (SPE) cartridge, and the concentration of pemetrexed was measured through liquid chromatography/mass spectrometry (LC/MS).

Figure 2:
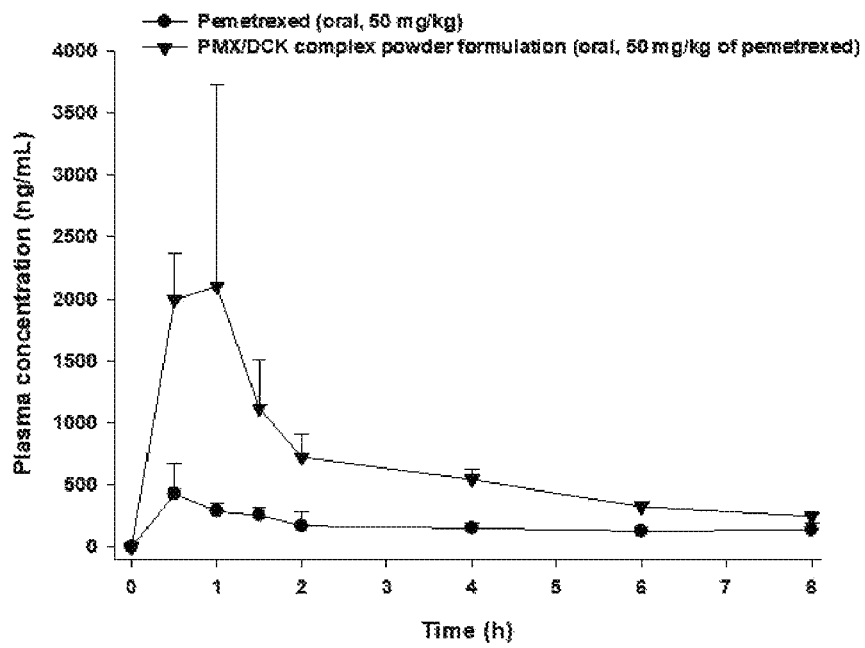
FIG. 2 shows the blood drug concentration over time after oral administration of 50 mg/kg pemetrexed or a capsule or tablet composition including a PMX/DCK ion-binding complex of Example 3, corresponding to 50 mg/kg pemetrexed, into rats.

FIGS. 1 and 2 show venous plasma pemetrexed concentration-time profiles after intravenous injection (5 mg/kg) and oral administration (50 mg/kg) of pemetrexed into rats or after oral administration of the tablet or capsule composition including the PMX/DCK ion-binding complex of Example 3 (corresponding to 50 mg/kg pemetrexed) into rats. Each value represents mean±standard deviation (n=4 in each group). As shown in FIG. 2, after oral administration of 50 mg/kg pemetrexed, $C_{max}$ was 451.78±221.38 ng/ml, $AUC_{last}$ was 1,393.3±395.12 ng·h/ml, and oral bioavailability compared to intravenous injection was evaluated to be 1.49%±0.42%. On the other hand, as shown in Table 4, when the tablet or capsule composition including the PMX/DCK ion-binding complex of Example 3, corresponding to 50 mg/kg pemetrexed, was orally administered, $C_{max}$ was increased 6.15 times (2,779.8±1,051.3 ng/ml), $AUC_{last}$ was increased 3.94 times (5,490.2±1,013.4 ng·h/ml) and oral bioavailability was increased 3.94 times (5.86%±1.08%), compared to when pemetrexed was orally administered alone. Therefore, the intestinal membrane permeability and oral absorption rate of pemetrexed in rats were significantly increased by the formation of the ion-binding complex with the bile acid derivative.

TABLE 4

| Sample | Pemetrexed | Pemetrexed | Tablet and capsule composition including PMX/DCK (Example 3) |
| --- | --- | --- | --- |
| Administration route | Intravenous injection | Oral | Oral |
| Pemetrexed dose (mg/kg) | 5 | 50 | 50 |
| $T_{max}$ (h) | — | 0.83 ± 0.58 | 0.67 ± 0.29 |
| $T_{1/2}$ (h) | 0.35 ± 0.08 | 6.06 ± 1.83 | 4.10 ± 1.40 |
| $C_{max}$ (ng/ml) | 15,318 ± 6100.3 | 451.78 ± 221.38 | 2,779.8 ± 1,051.3 |
| $AUC_{last}$ (ng · h/ml) | 9,377.5 ± 4,169.4 | 1,393.3 ± 395.12 | 5,490.2 ± 1,013.4 |
| $AUC_{inf}$ (ng · h/ml) | 9,414.5 ± 4,223.6 | 2,559.0 ± 755.48 | 6,988.4 ± 1,625.2 |
| Bioavailability (%) | 100 | 1.49 ± 0.42 | 5.86 ± 1.08 |

{in Table 4, $T_{max}$: time to reach maximum plasma drug concentration; $T_{1/2}$: plasma drug concentration half-life; $C_{max}$: maximum plasma drug concentration; $AUC_{last}$: area under plasma drug concentration-time curve up to final plasma drug concentration measurement time; $AUC_{inf}$: area under plasma drug concentration-time curve up to infinite time; bioavailability: ($AUC_{last,oral\ administration}$/oral dose)/($AUC_{last,intravenous\ injection}$/intravenous injection dose) × 100}

Example 11: Measurement of In-Vivo Bioavailability of Oral Nanoemulsion Including PMX/DCK Ion-Binding Complex Each of pemetrexed and an oral nanoemulsion composition including the PMX/DCK ion-binding complex prepared in Example 5 was dissolved in distilled water and then orally administered in an amount of 500 μl into rats. Separately, in order to evaluate oral bioavailability, a solution of pemetrexed in distilled water was injected in an amount of 200 μl into rats through the tail vein thereof. Blood samples (200 μl) were collected at scheduled times after drug administration and immediately mixed with 50 μl of a sodium citrate (3.8%) solution. The collected blood samples were centrifuged at 2,500×g and 4° C. for 15 min, pemetrexed in plasma was extracted using a solid-phase extraction (SPE) cartridge, and the concentration of pemetrexed was measured through liquid chromatography/mass spectrometry (LC/MS).

Figure 3:
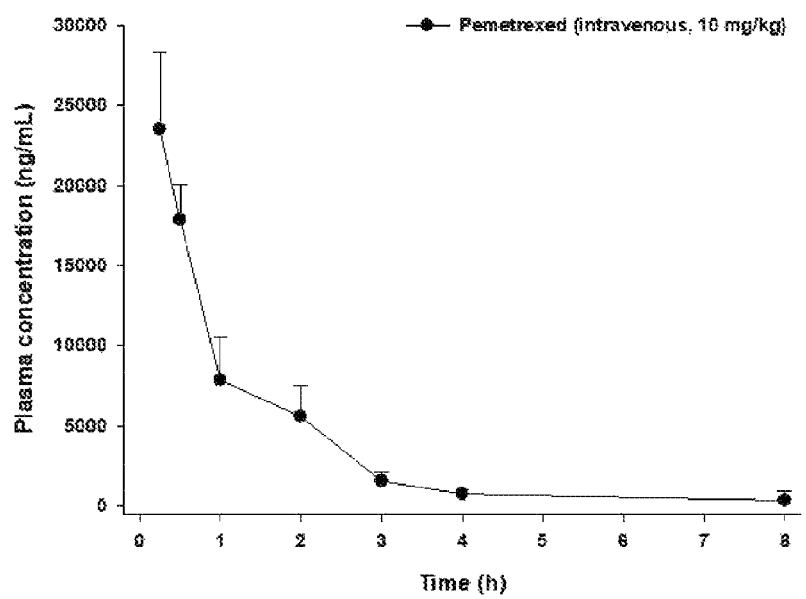
FIG. 3 shows the blood drug concentration over time after intravenous injection of 10 mg/kg pemetrexed into rats.
Figure 4:
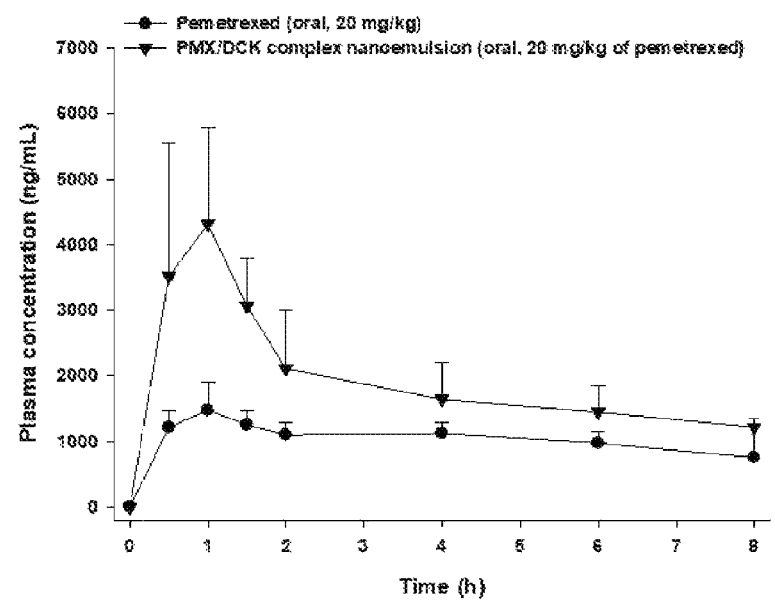
FIG. 4 shows the blood drug concentration over time after oral administration of 20 mg/kg pemetrexed or a nanoemulsion composition including a PMX/DCK ion-binding complex of Example 5, corresponding to 20 mg/kg pemetrexed, into rats.

FIGS. 3 and 4 show venous plasma pemetrexed concentration-time profiles after intravenous injection (10 mg/kg) and oral administration (20 mg/kg) of pemetrexed into rats or after oral administration of the nanoemulsion composition including the PMX/DCK ion-binding complex of Example 5 (corresponding to 20 mg/kg pemetrexed) into rats. Each value represents mean±standard deviation (n=4 in each group). As shown in FIG. 4, after oral administration of 20 mg/kg pemetrexed, $C_{max}$ was 1,487±332 ng/ml, $AUC_{last}$ was 7,546±938 ng·h/ml, and oral bioavailability compared to intravenous injection was 12.0%±1.50%. On the other hand, as shown in Table 5, when the nanoemulsion composition including the PMX/DCK ion-binding complex of Example 5, corresponding to 20 mg/kg pemetrexed, was orally administered, $C_{max}$ was increased 3.23 times (4,802±579 ng/ml), $AUC_{last}$ was increased 2.23 times (16,810±1,868 ng·h/ml) and oral bioavailability was increased 2.23 times (26.8%±2.98%) compared to when pemetrexed was orally administered alone. Therefore, the intestinal membrane permeability and oral absorption rate of pemetrexed in rats were significantly increased by the formation of the ion-binding complex with the bile acid derivative and by the nanoemulsion composition.

TABLE 5

| Sample | Pemetrexed | Pemetrexed | Nanoemulsion composition including PMX/DCK (Example 5) |
|---|---|---|---|
| Administration route | Intravenous injection | Oral | Oral |
| Pemetrexed dose (mg/kg) | 10 | 20 | 20 |
| $T_{max}$ (h) | — | 2.75 ± 3.50 | 0.90 ± 0.22 |
| $T_{1/2}$ (h) | 0.57 ± 0.07 | 7.55 ± 0.94 | 7.74 ± 2.74 |
| $C_{max}$ (ng/ml) | 32,220 ± 13,900 | 1,487 ± 332 | 4,802 ± 579 |
| $AUC_{last}$ (ng · h/ml) | 31,340 ± 5,342 | 7,546 ± 938 | 16,810 ± 1,868 |
| $AUC_{inf}$ (ng · h/ml) | 29,390 ± 4,844 | 14,300 ± 2,272 | 30,870 ± 2,831 |
| Bioavailability (%) | 100 | 12.0 ± 1.50 | 26.8 ± 3.00 |

{in Table 5: T: time to reach maximum plasma drug concentration; $T_{1/2}$: plasma drug concentration half-life; $C_{max}$: maximum plasma drug concentration; $AUC_{last}$: area under plasma drug concentration-time curve up to final plasma drug concentration measurement time; $AUC_{inf}$: area under plasma drug concentration-time curve up to infinite time; bioavailability: ($AUC_{last,oral\ administration}$/oral dose)/$AUC_{last,intravenous\ injection}$/intravenous injection dose) × 100}

Although the embodiments of the present invention have been disclosed for illustrative purposes, those skilled in the art will appreciate that various modifications are possible without departing from the technical idea of the present invention. Therefore, the embodiments disclosed in the present specification should be understood to be non-limiting and illustrative in every way, and are not to be construed as limiting the spirit or scope of the present invention. The scope of the present invention should be interpreted by the appended claims, and it will be understood that all technologies within the scope equivalent thereto belong to the scope of the present invention.

The invention claimed is:

1. An oral pharmaceutical composition, comprising an ion-binding complex comprising pemetrexed, a positively charged bile acid derivative and poloxamer, wherein the bile acid derivative is $N^{\alpha}$-deoxycholyl-L-lysyl-methylester (DCK).

2. The oral pharmaceutical composition of claim 1, wherein the DCK is used in an amount of 0.5 to 5 moles based on 1 mole of pemetrexed.

* * * * *